United States Patent [19]
Mathies et al.

[11] Patent Number: 5,728,528
[45] Date of Patent: Mar. 17, 1998

[54] UNIVERSAL SPACER/ENERGY TRANSFER DYES

[75] Inventors: Richard A. Mathies; Alexander N. Glazer; Jingyue Ju, all of Berkeley, Calif.

[73] Assignee: The Regents of the University of California, Oakland, Calif.

[21] Appl. No.: 531,132

[22] Filed: Sep. 20, 1995

[51] Int. Cl.$^6$ .......................... C12Q 1/68; C07H 21/04; C07H 21/02; C12P 19/34
[52] U.S. Cl. .......................... 435/6; 435/91.1; 435/810; 536/6.2; 536/18.4; 536/22.1; 536/25.32
[58] Field of Search .................. 435/6, 810, 91.1; 536/25.32, 6.2, 22.1, 18.4

[56] References Cited

U.S. PATENT DOCUMENTS

| | | | |
|---|---|---|---|
| 4,996,143 | 2/1991 | Heller et al. | 435/6 |
| 5,326,692 | 7/1994 | Brinkley et al. | 435/6 |
| 5,565,322 | 10/1996 | Heller et al. | 435/6 |

FOREIGN PATENT DOCUMENTS

| | | |
|---|---|---|
| 0 731 178 A2 | 9/1996 | European Pat. Off. . |
| 41 19 075 A | 12/1992 | Germany . |
| WO 94/17397 | 8/1994 | WIPO . |
| WO 95/21266 | 8/1995 | WIPO . |

OTHER PUBLICATIONS

Millican et al., NUC. Acid Res. 12(19):7435–7453, 1984.
Ju et al., "Fluorescence Energy Transfer Dye–Labeled Primers for DNA Sequencing and Analysis", PNAS USA (1995), 92:4347–4351.
Wang et al., "Rapid Sizing of Short Tandem Repeat Alleles Using Capillary Array Electrophoresis and Energy–Transfer Fluorescent Primers", Anal. Chem. (1995), 1197–1203.
Huang et al., "DNA Sequencing Using Capillary Array Electrophoresis", Anal. Chem. (1992), 64:2149–2154.
Glazer and Stryer, "Fluorescent Tandem Phycobiliprotein Conjugates", Biophys. J. (1983), 43:383–386.

Parkurst and Parkhurst, "Donor–Acceptor Distance Distributions in a Double–Labeled Fluorescent Oligonucleotide Both as a Single Strand and in Duplexes", Biochemistry (1995), 34:293–300.

Parkhurst and Parkhurst, "Kinetic Studies by Fluorescence Resonance Energy Transfer Employing a Double–Labeled Oigonucleotide: Hybridiztion to the Oligonucleotide Complement and to Single–Stranded DNA", Biochemistry (1995), 34:285–292.

McKeown et al. "Generation of Minisatellite Variant Repeat Codes on an Automated DNA Sequencer Using Fluorescent Dye–Labeled Primers", Short Technical Reports (1994), vol. 17, No. 5.

Fregeau and Fourney, "DNA Typing with Fluorescently Tagged Short Tandem Repeats: A Sensitive and Accurate Approach to Human Identification", Research Report (1993), 15:102–119.

Primary Examiner—W. Gary Jones
Assistant Examiner—Paul B. Tran
Attorney, Agent, or Firm—Townsend and Townsend and Crew LLP

[57] ABSTRACT

Fluorescent labels are provided employing energy absorber/donor components and energy acceptor/fluorescer components joined together by a spacer which comprises sugar phosphate monomeric units, particularly ribosyl phosphate monomeric units, where the sugar groups are free of active hydroxyl groups. Particularly, an energy transfer component is substituted at the 5' position of the spacer chain, while the other energy transfer component is substituted at the 1' position of the 3' terminal ribosyl group of the label forming an ET cassette for linking to a nucleic acid sequence with any compositions. By employing combinations of ET components, with a common energy absorber/donor and different fluorescers, one can provide for families of labels which can be tagged to any target molecules and which can be excited at a single wavelength and fluoresce at different wavelengths with large Stokes shifts. The compositions find particular application in sequencing.

21 Claims, 3 Drawing Sheets

UNIVERSAL SPACER/ENERGY TRANSFER DYES

INTRODUCTION

1. Technical Field

The technical field of this invention is fluorescent labels.

2. Background

There is an increasing demand to be able to identify and quantify components of mixtures. The greater the complexity of the mixture, the greater the interest in being able to simultaneously detect a plurality of the components present. As illustrative of this situation is DNA sequencing, where it is desirable to efficiently excite from one to four fluorescently tagged components with a laser source at a single wavelength, while providing for fluorescent signal emission at a plurality of distinctive wavelengths. In this situation, the different labels should not adversely affect the electrophoretic mobility of the sequences to which they are attached.

Currently, there are four methods used for automated DNA sequencing: (1) the DNA fragments are labeled with one fluorophore and then the fragments run in adjacent sequencing lanes (Ansorge et al., *Nucleic Acids Res.* 15:4593–4602 (1987)); (2) the DNA fragments are labeled with four different fluorophores and all the fragments are electrophoretically separated and detected in a single lane (Smith et al., *Nature* 321:674–679 (1986)); (3) each of the dideoxynucleosides in the termination reaction is labeled with a different fluorophore and the four sets of fragments are run in the same lane (Prober et al., *Science* 238:336–341 (1986)); or (4) the sets of DNA fragments are labeled with two different fluorophores and the DNA sequences coded with the dye ratios (Huang et al., *Anal Chem.* 64:2149–2154 (1992)).

All of these techniques have significant deficiencies. Method 1 has the potential problems of lane-to-lane variations in mobility, as well as a low throughput. Methods 2, 3, and 4 require that the dyes be well excited by one laser source and that they have distinctly different emission spectra. In practice, it is very difficult to find two or more dyes that can be efficiently excited with a single laser and that emit well separated fluorescent signals. As one selects dyes with distinctive red-shifted emission spectra, their absorption maxima will also move to the red and all the dyes can no longer be efficiently excited by the same laser source. Also, as more different dyes are selected, it becomes more difficult to select all the dyes such that they cause the same mobility shift of the labeled molecules.

It is therefore of substantial interest that improved methods be provided which allow for multiplexing of samples, so that a plurality of components can be determined in the same system and in a single run. It is also desirable for each label to have strong absorption at a common wavelength, to have a high quantum yield for fluorescence, to have a large Stokes shift of the emission, that the various emissions be distinctive, and that the labels introduce the same mobility shift. It is difficult to accomplish these conflicting goals by simply labeling the molecules with a single dye.

3. Relevant Literature

Ju et al., *Proc. Natl. Acad. Sci. USA* 92:4347–4351 (1995), and Ju et al., *Anal. Biochem.*, in press (1995) describe fluorescent energy-transfer (ET) primers for DNA sequencing. Also of interest is Wang et al., *Anal. Chem.* 67:1197–1203 (1995) which describes the use of ET primers for PCR product labeling and detection.

SUMMARY OF THE INVENTION

Fluorescent label compositions are provided comprising a combination of an energy absorber/donor component and an energy acceptor/fluorescer component bonded to a spacer comprising sugar phosphate links free of purine and pyrimidine bases forming an ET cassette. By providing a plurality of fluorescent dye compositions, having the same absorber/donor and different energy acceptor/fluorescer components, a family of fluorescent dye compositions (ET cassette) are provided which can label target molecules with any sequences and, which can be excited at the same wavelength, emit at widely spaced wavelengths, and provide for the same effect on mobility in electrophoresis, when associated with different nucleic acids. Also, the compositions can be readily synthesized using conventional polynucleotide synthetic chemistries.

DESCRIPTION OF THE SPECIFIC EMBODIMENTS

Novel fluorescent compositions, kits comprising the compositions, and methods of use are provided. The compositions comprise an energy absorber/donor component and an energy acceptor/fluorescer component joined together by a spacer comprising sugar, e.g., ribosyl phosphate links, where the hydroxyl at the 1'-position is substituted by hydrogen or etherified. The fluorescent compounds are useful as labels, particularly in association with nucleic acids. By employing a plurality of the compounds, where the compounds share a common energy absorber/donor component and common spacers, but vary as to the energy acceptor/fluorescer component, one can provide for a family of fluorescent labels which can be excited at the same wavelength and provide for widely spaced emission wavelengths. The family of compounds find particular use for labeling nucleic acids to be separated by electrophoresis, particularly exemplified by nucleic acid sequencing.

The subject labels will be characterized by having an energy absorber/donor component bonded to a spacer having at least three sugar-phosphate units and an energy acceptor/fluorescer component bonded to the spacer separated from the donor component by at least three sugar-phosphate units. The spacer with the donor and acceptor attached forms an ET cassette which can be used to tag any target molecules. One terminus of the label will have a functionality for reacting with a phosphate or hydroxyl, particularly of a nucleoside or nucleotide, normally the only functionality available for reacting. Generally, the number of sugar-phosphate moieties will be not greater than 15, usually not greater than 12, preferably not greater than about 9, and at least 3, preferably at least about 4, more usually in the range of about 5–8. While various sugars may be employed of from 5–6 carbon atoms, conveniently the sugar employed is ribose. Two of the hydroxyl groups of the sugar will be involved in the phosphate ester linkages while the remaining hydroxyl groups, except for the hydroxyl group at 1'-position, will either be substituted, particularly etherified by alkyl of from 1-3 carbon atoms, so as to be chemically inert, or replaced with hydrogen. The 1'-position may serve as a site for linking to an energy transfer component or will be modified so as to be unreactive as described above. Particularly of interest as the sugar used in the spacer will be 1', 2'-dideoxy ribose, where the 3' and 5' positions will serve as phosphate ester sites in the chain. If desired, the terminal 5' position may be used as the site for linking to one of the energy transfer components.

The energy transfer ("ET") components may be at any sites of the spacer which allow for efficient energy transfer. Therefore, the energy transfer components will generally be spaced apart for about 3-9, more usually for about 4-8 sugar phosphate moieties. The particular spacing is not critical to this invention, so long as a similar spacing is used for each compound to be used in combination. Conveniently, the 5' terminal hydroxyl group may be the site for one of the energy transfer components, particularly the donor energy transfer component. Also, the other component will be conveniently substituted at a 1'-position, either directly or through a linking group of not more than about 20 atoms, more usually not more than about 12 atoms, where a cyclic intervening group is present, the shorter number of atoms around the ring being counted.

The linking group can be varied widely and is not critical to this invention. The linking groups may be aliphatic, alicyclic, aromatic or heterocyclic, or combinations thereof. Functionalities or heteroatoms which may be present in the linking group include oxygen, nitrogen, sulfur, or the like, where the heteroatom functionality which may be present is oxy, oxo, thio, thiono, amino, amido, and the like. Any of a variety of linking groups may be employed which do not interfere with the energy transfer and gel electrophoresis, which may include purines or pyrimidines, particularly uridine, thymidine, cytosine, where substitution will be at an annular member, particularly carbon, or on a side chain, e.g. methyl in thymidine. The ET component may be bonded directly to the base or through a linking group of from 1 to 6, more usually from 1 to 3 atoms, particularly carbon atoms. The linking group may be saturated or unsaturated, usually having not more than about one site of aliphatic unsaturation.

For the ET component linked to the 1'-position, one may advantageously use the base of a nucleotide as the site for linking the ET component, the 1'-hydroxyl of the sugar, or one may introduce a functionality at the 1'-position, such as amino, carboxyl, and the like. The functionality of the 1'-position may be extended, particularly with a substituted alkylene group of from 2-8, usually 2-6 carbon atoms where the final functionality will depend upon the available functionality present on the ET component. Usually, the functionality for linking to the ET component will be carboxyl or amino.

Linkages which may be involved include amino (for example, by reductive amination), amide, ethers, either oxy or thio, esters, or the like. The fluorescent label comprising the ET components may be bonded to the nucleic acid molecule by any convenient linkage, usually a phosphate ester linkage. The subject fluorescent label molecules will normally be at the 5' terminus of the nucleic acid molecule, but in certain situations may be at a different site if desired. For use in sequencing, the subject compositions will normally be at the 5' end of the sequence.

The compositions of interest will, for the most part, have the following formula Wherein:
D is the donor component;
A is the acceptor component;
S is the spacer monomer;
S' is a modified spacer monomer, where the modification is at the 1'-position for linkage to A;
X is the target molecule to be labeled, which can be polynucleotides, polypeptides or the like. X contains an activated phosphate group for reaction with an hydroxyl, protected hydroxyl, or a mono- or polynucleotide particularly a deoxyribonucleotide, generally of from 1-30, more usually of from 1-20 nucleotides; and n is in the range of 2-14, more usually in the range of 4-7.

The energy donors will generally be compounds which absorb in the range of about 300-800 nm more usually in the range of about 450-700 nm, and are capable of transferring energy to a fluorescer, which fluorescer generally absorbs light of a wavelength 15 nm. more usually 20 nm or higher, than the absorption wavelength of the donor. The fluorescers will generally emit in the range of about 400-900 nm. A wide variety of energy absorbers may be employed, such as fluorescein, BODIPY, DAPI, Indo-1, coumarin, dansyl, cyanine dyes, or the like. Energy acceptors/fluorescers may include some of the compounds indicated above, which fluoresce at or above about 450 nm, as well as compounds such as rhodamines, fura-2, and diverse cyanine dyes. For the most part, the ET components will be non-intercalating, stable under the conditions of electrophoresis, and have high extinction coefficients and high fluorescence efficiency.

The energy donor will have a strong molar absorbance coefficient at the desired excitation wavelength, desirably greater than about $10^4$, preferably greater than about $10^5$ $cm^{-1}M^{-1}$. The excitation maximum of the donor and the emission maximum of the acceptor will be separated by at least about 15 nm or greater. The spectral overlap integral between the emission spectrum of the donor and the absorption spectrum of the acceptor chromophore and the distance between the chromophores will be such that the efficiency of energy transfer from donor to acceptor will typically range from about 20 to 100%. For the most part, the donor-acceptor dyes will have molecular weights of less than about 2 kD, generally less than about 1.5 kD.

While for the most part, single pairs of ET components will be used, there can be situations where up to three different chromophores will be utilized in sets, usually differing by not more than two different chromophores. That is, normally the energy donor is the same and the final fluorescer and one other intermediate chromophore will be different. By using more ET components, one may greatly extend the Stokes shift, so that one may excite in the visible wavelength range and have emission in the infra-red wavelength range, usually below about 1,000 nm, more usually below about 900 nm. Detecting light in the infra-red wavelength range has many advantages, since it will not be subject to interference from Raman and Rayleigh light resulting from the excitation light and the background emission signals from biological samples are lower in the red. In order to maintain the mobility constant, one may use the same number of ET components on each of the labels, having two to three of the same ET components on each of the labels.

Where the subject labels are used as primers, they can have nucleotide sequences of from about 8-30, more usually from about 8–20 nucleotides, where the sequence is complementary to the desired priming site or priming site in various commercially available vectors. The vectors may include single-stranded filamentous bacteriophage vectors, the bacteriophage lambda vector, Charon vectors, pUC vectors, pGEM vectors, or the like. Thus, the subject labels would be extended from the common sequence of the vector into the cloned sequence. For example, universal primers may be prepared, where the primer may be any one of the universal primers, having been modified by bonding of the label to the primer. Thus, various commercial primers are available, such as primers from pUC/M13, λgt10, λgt11, and the like. See, Sambrook et al., *Molecular Cloning: A Laboratory Manual*, 2nd ed., CSHL, 1989, Section 13.

The subject invention finds particular application with nucleic acid chains, where the nucleic acid chains find use as primers in sequencing, the polymerase chain reaction, particularly for sizing, or other systems where primers are employed for nucleic acid extension and one wishes to distinguish between various components of a mixture as related to the particular labels. For example, in sequencing, universal primers may be employed, where a different pair of ET components is used for each of the different dideoxynucleotides used for the extension during the sequencing reaction. DNA sequences are cloned in an appropriate vector having a primer sequence joined to the sequence to be determined. Different 2', 3'-ddNTPs are employed, so that termination occurs at different sites, depending upon the particular ddNTP which is present in the chain extension. By employing the subject primers, each ddNTP will be associated with a particular label. After extension with the Klenow fragment, the resulting fragments may then be separated in a single lane by electrophoresis or in a single capillary by electrophoresis, where one can detect the terminating nucleotide by virtue of the fluorescence of the label.

The subject compounds may have an active phosphate for linking to a nucleotide. Various active phosphates include phosphoamidites, where the oxygen is substituted with an alkyl group of from 1–3 carbon atoms, cyanoalkyl, particularly of from 2–3 carbon atoms, etc. The amino group will generally be dialkylated where the alkyl groups will be from 1–4, more usually 2–3 carbon atoms. Alternatively, phosphite esters may be employed, where the available oxygens will be substituted with alkyl groups of from 1–3 carbon atoms.

The subject compounds may be readily synthesized in accordance with conventional techniques, where the synthesis follows conventional synthetic procedures for nucleotides. Thus, one can readily oligomerize 1'-Y 3'-activated, 5'-protected 2'-deoxyribose in the same manner as DNA is synthesized, where Y is hydrogen, a functional group, or an ET component joined directly or through a linking group.

Kits are provided having combinations of labels, usually at least 2. Each of the labels will have the donor-acceptor pair, usually with the same backbones, where the labels will be separated along the backbone and give comparable mobility in the separation method to be used. Each of the labels in a group to be used together will absorb at about the same wavelength and emit at different wavelengths. Each of the labels in the group will have about the same effect on mobility in the separation method.

The kits will generally have up to about 6, usually about up to about 4 different labels which are matching, but may have 2 or more sets of matching labels, having 2–6 different labels.

The following examples are offered by way of illustration and not by way of limitation.

EXPERIMENTAL

Design and Synthesis of Energy Transfer Fluorescent Dye Tagged Oligonucleotide Labels with a Universal Spacer The M13 (−21) universal primer containing 18-nucleotides with the following sequence (SEQ ID NO:2)

were synthesized with donor-acceptor fluorophore pairs separated by six 1', 2'-dideoxyribose phosphates (S) which were introduced using 5'-dimethoxytrityl-1', 2'-dideoxyribose-3'-[(2-cyanoethyl)-(N,N-diisopropyl)]-phosphoramidite (dSpacer CE Phosphoramidite, Glen Research) (Structure 1) on a DNA synthesizer Structure 1.
dSpacer CE Phosphoramidite

The 18-mer contains a modified base T* introduced by the use of 5'-dimethoxytrityl-5-[N-(trifluoroacetylaminohexyl)-3-acrylimido]-2'-deoxyUridine, 3'-[(2-cyanoethyl)-(N,N-diisopropyl)]-phosphoramidite (Amino-Modifier C6 dT, Glen Research) (Structure 2).

Structure 2.
Amino-Modifier C6 dT which has a protected primary amine linker arm at the C-5 position. The T* was attached to the 5' end of the nucleotide sequences before the spacer. The donor dye was attached to the end of the spacer on the 5' side of the oligomer, and the acceptor dye was attached to the primary amine group on the T*. The primers are denoted as D-S$_6$-A (ET cassette), where D is the donor, A is the acceptor and S$_6$ indicates the number of spacing sugars between D and A. In all the primers prepared, D=FAM(F), a fluorescein derivative; A=FAM(F), JOE(J), TAMRA(T) or ROX(R) with the last two being rhodamine derivatives. We have also found that carboxyrhodamine-6G is a good substitute of JOE (FAM: 6-carboxyfluorescein; JOE: 2' 7'-dimethoxy-4', 5'-dichloro-6-carboxyfluorescein, TAMRA: N, N, N', N'-tetramethyl-6-carboxyrhodamine; ROX: 6-carboxy-X-rhodamine). As a representative example, the structure of FS$_6$T is shown below (Structure 3) (SEQ ID NO:3).

Structure 3.
FS₆T (SEQ ID NO: 3)

FAM: abs, 495 nm; em, 525 nm

TAMRA: abs, 555 nm; em, 580 nm

The advantages of the energy transfer approach described here are (1) that primers with any sequences can be labeled with ET coupled dyes simply by introducing a T* using Amino modifier dT or other phosphoramidite such as Amine-VN Phosphoramidite (CLONTECH) (Structure 4) at the 5' end of the oligonucleotide sequences, and then six 1', 2'-dideoxyribose phosphates using dSpacer. Donor and fluorescer dyes can be easily attached to this scaffold

Structure 4.
Amine-VN Phosphoramidite forming an ET cassette; (2) a large Stokes shift and much stronger fluorescence signals can be generated when exciting at 488 nm and (3) no mobility shift adjustment on the 4-color data of the DNA sequencing fragments extended from the FS₆(F,J,T,R) primers are needed to call sequences.

Figure 1A:
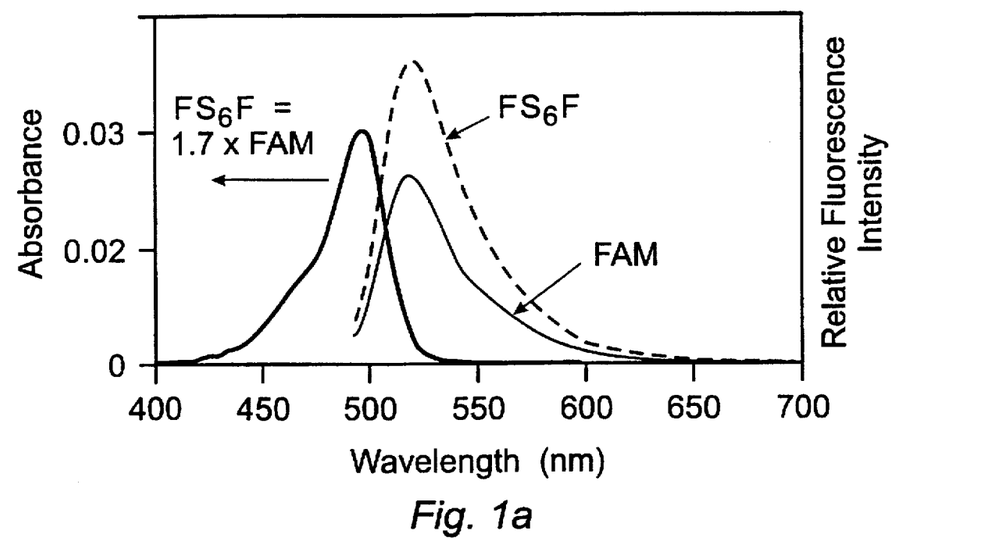
FIGS. 1a, 1b, 1c, and 1d show the comparison of the fluorescence emission intensity of four energy transfer (ET) primers, respectively.
Figure 1B:
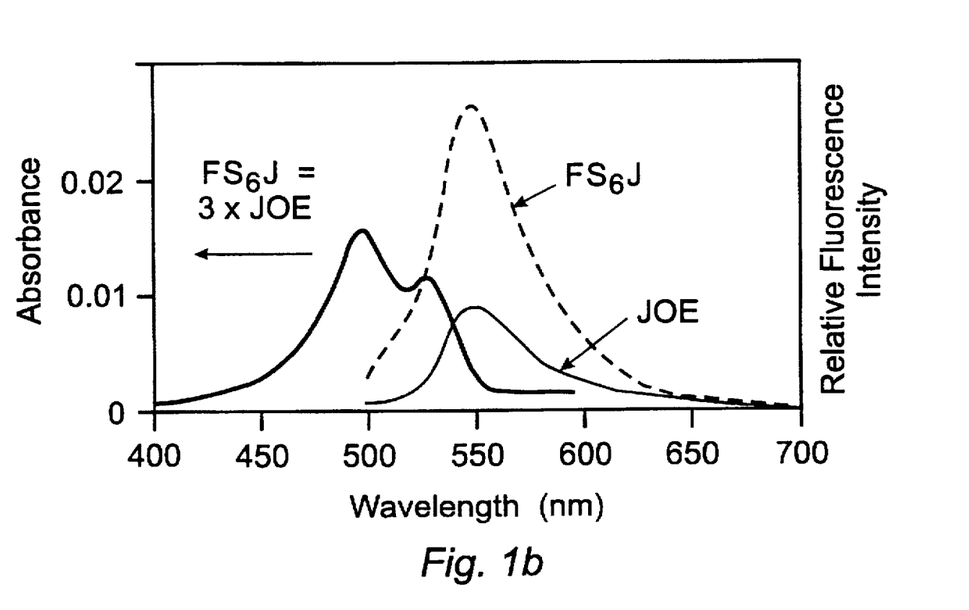
Figure 1C:
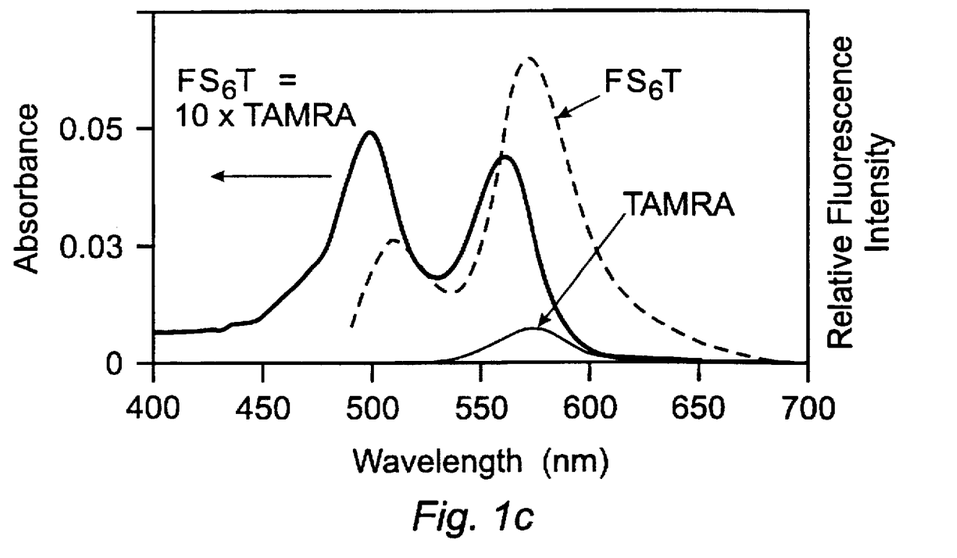
Figure 1D:
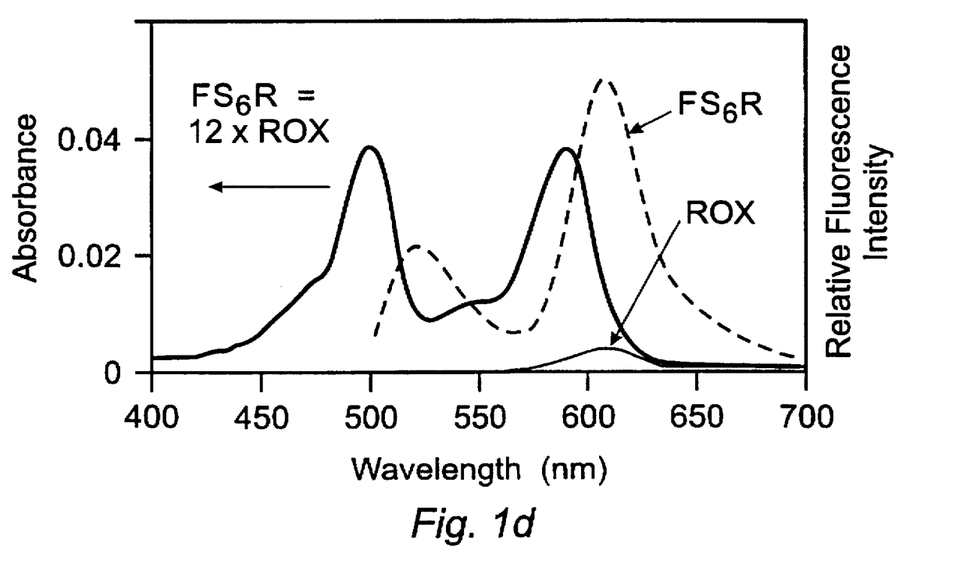

The absorption and emission spectra of the ET primers are presented in FIGS. 1a, 1b, 1c, and 1d. Each ET primer exhibits the characteristic absorption of FAM at 496 nm as well as strong absorption at 525 nm due to JOE in FS₆J, at 555 nm due to TAMRA in FS₆T and at 585 nm due to ROX in FS₆R. The fluorescence emission spectra of the ET primers are dominated by the acceptor emissions. While the emission maximum of FS₆F is at 525 nm, the emission of FS₆J with 488 nm excitation is Stokes-shifted to 555 nm, that of FS₆T is shifted to 580 nm, and that of FS₆R is shifted to 605 nm. In the case of FS₆R, the Stokes shift is over 100 nm. FIG. 1a, 1b, 1c, and 1d also present emission spectra of the single dye-labeled primers measured at the same molar concentration as that of the corresponding ET primers. Substantial enhancement of the ET primer emission intensity is observed compared to the corresponding single dye-labeled primers, indicating that efficient energy transfer is occurring. The fluorescence intensity improvements derived from FIG. 1 are: FS₆F=1.7×FAM (FIG. 1a); FS₆J=3×JOE (FIG. 1b); FS₆T=10×TAMRA (FIG. 1c); FS₆R=12×ROX (FIG. 1d).

DNA Sequencing with ET (FS₆F, FS₆J, FS₆T, FS₆R) Primers

Figure 2:
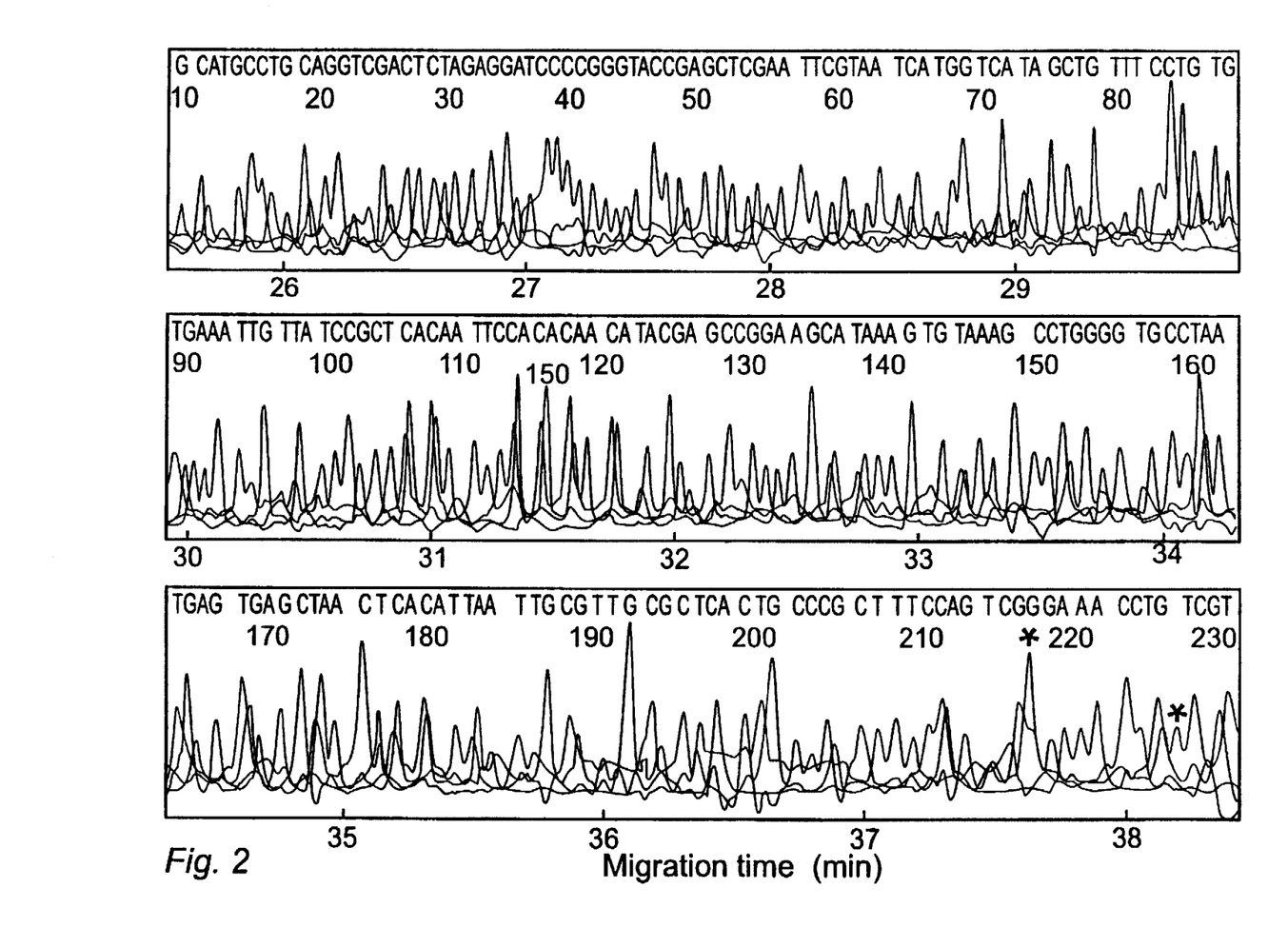
FIG. 2 shows a portion of 4-color analyzed data (nucleotides 10 to 230); SEQ ID NO:1 of DNA sequencing profile of M13mp18 DNA using the ET primer $FS_6F$, $FS_6J$, $FS_6T$, $FS_6R$ and Sequenase 2.0. Primer concentration: 0.4 pmol; DNA template: 1.6 µg (0.4 µg for each base extension). The CE sequencing protocols were similar as described (Ju et al., *Anal. Biochem.*, in press (1995)).

The successful application of the ET dye-labeled primers using the universal spacer for DNA sequencing was also realized. The primers were shown to be good substrates for the DNA polymerase without any anomalies. FIG. 2 shows a portion of 4-color DNA sequencing data (10–230 nucleotides) using the FS₆N primer set. The reaction was performed using equal amounts of primer (0.4 pmol) and 0.4 µg of template DNA for each base extension. The 4-color CE sequencing profile was obtained after simply applying a matrix transformation on the raw data to correct for the crosstalk between the four channels. The sequence can be called without applying any mobility shift adjustment. The analysis of these data using more sophisticated peak calling software should lead to even better base calling and longer reads.

It is evident that with the universal spacer (ET cassette) method described above, we are able to synthesize broad families of dye-labeled biopolymers or other target molecules having a common donor and 2, 3, 4 or more different acceptors. With this approach, all the oligonucleotide primers and probes for sequencing, PCR and hybridization etc. can be tagged with ET coupled dyes. Such classes of donor-acceptor labeled molecules find wide application in multiple-color genetic analyses.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method for identifying different nucleic acid sequences using a combination of fluorescent labels in an electrophoresis separation, said fluorescent labels fluorescing at different wavelengths and each different label joined to a different nucleic acid sequence, the improvement which comprises:

said labels comprising an energy donor component absorbing at a common wavelength, an acceptor component absorbing energy transferred by said energy donor component, where the acceptor for each label emits at a different wavelength, and said energy donor component and acceptor component linked by a backbone comprising sugar phosphate ester monomer linkages with the 1'-hydroxyl group being replaced with a hydrogen or etherified.

2. A method according to claim 1, wherein said sugar phosphate ester linkages are 1',2'-dideoxyribosyl-3', 5'-phosphate linkages.

3. A method according to claim 2, wherein said backbone comprises 3 to 15 phosphate ester monomers.

4. A method according to claim 3, wherein said backbone has a 5' hydroxyl terminus and said energy donor component is linked at said 5' terminus.

5. A method according to claim 3, wherein said backbone has a 3' terminus comprising a linking functionality at the 1'-position of said 1', 2'-dideoxyribosyl group to which said acceptor is covalently bonded.

6. In a method for identifying different nucleic acid sequences using a combination of fluorescent labels in an electrophoresis separation, said fluorescent labels linked to the appropriate primers and fluorescing at different wavelengths and each different label joined to a different nucleic acid sequence, the improvement which comprises:

said labels comprising an energy donor component absorbing at a common wavelength, an acceptor component absorbing energy transferred by said donor component, where the acceptor for each label emits at a different wavelength, and said energy donor component and acceptor component are linked by a backbone comprising from 3 to 15 1',2'-dideoxyribosyl 3',5'-phosphate ester monomer linkages, said energy donor component covalently linked at the 5' terminus of said backbone and said acceptor component linked to the 1'-position of the 3'-terminal 1',2'-dideoxyribose of said backbone.

7. A method according to claim 6, wherein said backbone comprises from 5 to 8 1', 2'-dideoxyribosyl 3', 5'-phosphate ester monomer linkages.

8. A method according to claim 6, wherein said donor component is a fluorescein.

9. A method according to claim 6, wherein said acceptor is linked through a uridine.

10. A method according to claim 6, wherein said acceptor is linked through a carboxy group bonded to the 1'-position at the 3'-terminus of the sugar monomer.

11. A method according to claim 6, wherein at least one fluorescer is a rhodamine.

12. In a method for identifying different nucleic acid sequences using a combination of fluorescent labels in an electrophoresis separation for determining a nucleic acid sequence, where each of said labels is associated with the presence of a different nucleotide, said fluorescent labels fluorescing at different wavelengths and each different label joined to a different nucleic acid sequence, the improvement which comprises:

said labels comprising an energy donor component absorbing at a common wavelength, an acceptor component absorbing energy from said energy donor component, where the acceptor for each label emits at a different wavelength, and said energy donor component and acceptor component linked by a backbone comprising from 3 to 9 1', 2'-dideoxyribosyl 3', 5'-phosphate ester monomer linkages, said energy donor component covalently linked at the 5' terminus of said backbone and said acceptor component linked to the 1'-position of the 3'-terminal 1', 2'-dideoxyribose of said backbone.

13. A compound comprising an energy donor component and an acceptor component absorbing energy transferred by said energy donor component, said components linked by a backbone comprising sugar phosphate ester monomer linkages with the 1'-hydroxyl group being replaced by a hydrogen or etherified.

14. A compound according to claim 13, wherein said backbone comprises from 3 to 15 1', 2'-dideoxyribosyl 3', 5'-phosphate ester monomer linkages.

15. A compound according to claim 14, wherein said energy donor component is covalently bonded at the 5' backbone terminus and said acceptor is covalently bonded to the backbone 3'-terminal of 1', 2'-dideoxyribosyl 3', 5'-phosphate ester at the 1'-position through a linking group.

16. A compound according to claim 15, wherein the 3'-terminus of said backbone is an hydroxyl, protected hydroxyl, phosphoramidite, phosphite, nucleotide or oligonucleotide.

17. A compound of the formula 5'-fluorescein substituted poly-1', 2'-dideoxyribose-3', 5'-phosphate, having from 3 to 15 1', 2'-dideoxyribose-3', 5'-phosphate monomeric units, and substituted through a linking group at the 1'-position of the 3'-terminal 1', 2'-dideoxyribose-3', 5'-phosphate monomeric unit with a fluorescein or a rhodamine.

18. A compound according to claim 17, wherein the 3'-terminus of said backbone is an hydroxyl, protected hydroxyl, phosphoramidite, phosphite, nucleotide or oligonucleotide.

19. A compound according to claim 17, wherein said linking group is a carboxyl or uridyl group.

20. A kit comprising at least two compounds according to claim 13 differing in said acceptor and having the same energy donor.

21. A kit comprising at least two compounds according to claim 15 differing in said acceptor and having the same energy donor.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 221 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:1:

```
GCATGCCTGC AGGTCGACTC TAGAGGATCC CCGGGTACCG AGCTCGAATT CGTAATCATG      60

GTCATAGCTG TTTCCTGTGT GAAATTGTTA TCCGCTCACA ATTCCACACA ACATACGAGC     120

CGGAAGCATA AAGTGTAAAG CCTGGGGTGC CTAATGAGTG AGCTAACTCA CATTAATTGC     180

GTTGCGCTCA CTGCCCGCTT TCCAGTCGGG AAACCTGTCG T                        221
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA     ( i x ) FEATURE:
        ( A ) NAME/KEY: modified_base
        ( B ) LOCATION: 1
        ( D ) OTHER INFORMATION: /mod_base=OTHER
        / note= "N = 1',2'-dideoxyribose
        phosphate modified at the 5'-hydroxy
        with a donor energy transfer component"

( i x ) FEATURE:
        ( A ) NAME/KEY: modified_base
        ( B ) LOCATION: 2..6
        ( D ) OTHER INFORMATION: /mod_base=OTHER
        / note= "N = 1',2'-dideoxyribose
        phosphate"

( i x ) FEATURE:
        ( A ) NAME/KEY: modified_base
        ( B ) LOCATION: 7
        ( D ) OTHER INFORMATION: /mod_base=OTHER
        / note= "N = 2'-deoxyuridine modified at
        the primary amine group with an energy
        acceptor/fluorescer dye"

( x i ) SEQUENCE DESCRIPTION: SEQ ID NO:2:

```
NNNNNNNGTA AAACGACGGC CAGT                                            24
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA -continued

```
( i x ) FEATURE:
        ( A ) NAME/KEY: modified_base
        ( B ) LOCATION: 1
        ( D ) OTHER INFORMATION: /mod_base=OTHER
                / note= "N = 6-[(5'-(carboxy-6-aminohexyl-
                phosphato)- 1',2'-dideoxyribosyl)]
                fluorescein"

( i x ) FEATURE:
        ( A ) NAME/KEY: modified_base
        ( B ) LOCATION: 2..6
        ( D ) OTHER INFORMATION: /mod_base=OTHER
                / note= "N = 1',2'-dideoxyribose
                phosphate"

( i x ) FEATURE:
        ( A ) NAME/KEY: modified_base
        ( B ) LOCATION: 7
        ( D ) OTHER INFORMATION: /mod_base=OTHER
                / note= "N = 6-[(5-(N-(6-
                carboxyaminohexyl)-3-acrylamido)-2'-
                deoxyuridyl)]rhodamine"

( x i ) SEQUENCE DESCRIPTION: SEQ ID NO:3:

NNNNNNNGTA AAACGACGGC CAGT                                            2 4
```